United States Patent
Næstoft et al.

[11] Patent Number: 5,643,187
[45] Date of Patent: Jul. 1, 1997

[54] DRESSING

[75] Inventors: Roland Næstoft, Allerød; Hanne Jensen, Copenhagen, both of Denmark

[73] Assignee: Coloplast A/S, Denmark

[21] Appl. No.: 256,593

[22] PCT Filed: Jan. 15, 1993

[86] PCT No.: PCT/DK93/00011

§ 371 Date: Jan. 11, 1995

§ 102(e) Date: Jan. 11, 1995

[87] PCT Pub. No.: WO93/13813

PCT Pub. Date: Jul. 22, 1993

[30] Foreign Application Priority Data

Jan. 17, 1992 [DK] Denmark ............... 0054/92

[51] Int. Cl.⁶ ............................................. A61F 13/00
[52] U.S. Cl. ............................. 602/43; 602/52; 602/58
[58] Field of Search ........................... 602/43–47, 52, 602/54, 58

[56] References Cited

U.S. PATENT DOCUMENTS

| | | | |
|---|---|---|---|
| 2,785,677 | 3/1957 | Stumpf | 602/58 |
| 3,972,328 | 8/1976 | Chen | 128/156 |
| 4,285,338 | 8/1981 | Lemelson | 602/58 |
| 4,773,409 | 9/1988 | Cilento | 604/358 |
| 5,167,613 | 12/1992 | Karami | 602/58 |
| 5,188,124 | 2/1993 | Feret | 602/52 |
| 5,225,199 | 7/1993 | Hidaka | 602/58 |
| 5,322,695 | 6/1994 | Shah | 602/54 |
| 5,409,472 | 4/1995 | Rawlings | 602/58 |
| 5,413,567 | 5/1995 | Barth | 602/58 |

FOREIGN PATENT DOCUMENTS

| | | | |
|---|---|---|---|
| 147034 | 11/1978 | Denmark . | |
| 147035 | 3/1984 | Denmark . | |
| 154747 | 12/1988 | Denmark . | |
| 154806 | 12/1988 | Denmark . | |
| 157899 | 3/1990 | Denmark . | |
| 158493 | 5/1990 | Denmark . | |
| 0092999 | 11/1983 | European Pat. Off. | 602/58 |
| 97946 | 2/1984 | European Pat. Off. . | |
| 189999 | 8/1986 | European Pat. Off. . | |
| 0190814 | 8/1986 | European Pat. Off. . | |
| 0409587 | 1/1991 | European Pat. Off. . | |
| 409587 | 1/1991 | European Pat. Off. . | |
| 415183 | 10/1991 | European Pat. Off. . | |
| 156035 | 4/1987 | Norway . | |
| 157686 | 5/1989 | Norway . | |
| 365410 | 3/1974 | Sweden . | |
| 886894 | 11/1988 | WIPO . | |
| 9001911 | 3/1990 | WIPO . | |
| 9001915 | 3/1990 | WIPO . | |

OTHER PUBLICATIONS

Polymer Durometer Chart: Polyurethan—The Bridge Between Silicone Rubber and Plastics.

*Primary Examiner*—Michael Powell Buiz
*Assistant Examiner*—Chalin Smith
*Attorney, Agent, or Firm*—Ostrolenk, Faber, Gerb & Soffen, LLP

[57] ABSTRACT

A dressing comprising a skin friendly pressure-sensitive continuous or discontinuous adhesive layer (2), which is coated on one side with a non-adhesive flexible polymer film (1a) and which is optionally coated on the other side with a removable release layer (3), said polymer film (1a) consisting of an uppermost layer (4) of a material which is relatively hard, and a lowermost layer (5) of a material which is relatively soft, said lowermost layer (5) being thicker than the uppermost layer (4). The dressing has a low surface friction and a good flexibility.

22 Claims, 2 Drawing Sheets

DRESSING

BACKGROUND OF THE INVENTION

The present invention concerns a dressing of the type comprising a skin friendly pressure-sensitive continuous or discontinuous adhesive layer, which is coated on one side with a non-adhesive flexible polymer film, optionally with a flexible foam layer interposed between the film layer and the adhesive layer, and which is optionally coated on the other side with a removable release layer.

Dressings of the above-mentioned type are extensively used for the treatment of wounds, in particular cronic wounds, burns and surgical wounds. Dressings of the above-mentioned type are also used for the treatment of blisters, minor wounds and chafe wounds, as well as prophylactically to avoid the same, e.g. in connection with the practice of sports or manual labor and the like, where the skin areas, such as heels, elbows, knees and palms of the hand are subject to particularly severe stresses which easily give rise to the above-mentioned minor injures. Dressings of the above-mentioned type continue to find new fields of application. It may for example be mentioned that such dressings have also been found useful as a transcutaneous dosing means for the dosing of various medicaments, such as hormones or nicotine.

Thus, a large number of products of the above-mentioned type are known. The products most used are the so-called liquid absorbing bandages, e.g. hydrocolloid plasters and hydrogel plasters.

Hydrogel bandages consist of a liquid absorbing crosslinked polymer, such as collagen, polyvinyl alcohol and gelatine, as well as of a non-adhesive watertight film having a low water vapor permeability arranged on the side of the bandage which is not intended to face the skin of the patient.

A hydrogel bandage contains a large amount of water already prior to use. In the cases where the bandage is approximately saturated with water, the bandage is frequently not adhesive and must therefore be secured to the skin in another manner, e.g. by means of a plaster. An example of this is the so-called 2ND SKIN® dressing which is commercially available from Spenco Medical Ltd., U.K. Other hydrogel bandages having a lower content of water exhibit excellent adhesive properties. Certain modified gellable polymers, however, are capable of maintaining a reasonably good adhesive capability, even when they are essentially saturated with water.

Hydrogel bandages are known e.g. EP Patent Applications 97846 and 415183, SE Published Application 365 410, WO Patent Application 88/6894 and U.S. Patent Specification 4 093 673.

Hydrocolloid plasters normally consist of
(a) an adhesive material consisting of
  (i) a continuous phase containing an adhesive and composed of for example an elastomer, a plasticizer for elastomers, a tack promoting resin and optionally an oil based extender as well as an antioxidant, and
  (ii) a discontinuous phase dispersed therein and consisting of one or more water soluble or water swellable hydrocolloids, such as starch or cellulose derivatives or other hydrophillic polymers, and
(b) a non-adhesive watertight film arranged on the side of the bandage which is not intended to face the patient's skin.

Such a dressing is known e.g. from the DK Patent Specifications 147 034 and 147 035 (corresponding to U.S. Patent Specifications 4 231 369 and 4 367 632). The products mentioned in these consist of an adhesive material consisting of (I) a continuous phase containing
  (a) a physically cross-linked elastomer in the form of one or more styrene olefin styrene block copolymers or ethylene propylene block copolymers,
  (b) a hydrocarbon adhesive resin in the form of a polymer or copolymer of cyclopentadiene, dicyclopentadiene, α-pinene and/or β-pinene,
  (c) an antioxidant,
  (d) optionally an oil extender consisting of one or more mineral oils, and
  (e) an elastomer polar plasticizer, such as for example an ester of a polyethylene glycol or polypropylene glycol, or an ester of a di- or polybasic carboxylic acid with a preferably aliphatic alcohol, as well as (II) a phase dispersed in the continuous phase and consisting of one or more water swellable hydrocolloids.

Also other elastomers may occur in known dressings, e.g., natural rubber, synthetic resins of a nature similar to natural rubber and silicone rubbers. Further, polyisobutylene in a suitable molecular weight distribution is also frequently used as an adhesive material and texture imparting component in dressings, e.g. as stated in U.S. Patent Specification 3 339 546.

Other dressings of a similar type are known from NO Published Application 157 686 as well as DK Patent Specifications 154 806, 147 226, 157 899 and 154 747.

Mention should also be made of WO Patent Application 90/01911, and DK Published Application 158 493, which concern bandages that essentially do not contain components which are actively water absorbing. In particular, thin, non-liquid absorbing products are greatly used. Mention may here be made of e.g. the dressing Tegaderm® which is marketed by 3M, the dressing Bioclosure® which is marketed by Johnson & Johnson, the dressing Up-Site® which is marketed by Smith & Nephew, and the dressing Uniflex® which is marketed by Howmedica.

The thin non-absorbing products are extremely flexible and often transparent. They consist of a non-absorbing adhesive, such as rubber, various acrylates or copolymerisates thereof, polyvinyl ether and synthetic or natural resins and a film cover layer which is frequently watertight, but has a relatively great water vapor permeability. In contrast to the absorbing bandages, this water vapor permeability is very important, because the skin constantly secretes a certain amount of liquid which may give rise to maceration. In case of very suppurating wounds, these thin non-absorbing bandages cannot always be applied successfully.

A development of recent years is the combination of these different types of bandages. For example, also hydro-colloid bandages as thin as 0.3 mm are now available. Such thin hydrocolloid bandages are not always capable of absorbing all the liquid secreted from the skin and possible wounds, and it is thus important that these thin hydro-colloid bandages have a cover film with a reasonably great water vapor permeability. This water vapor permeability, as mentioned before, has no significant importance for the thicker hydro-colloid bandages of e.g. 1.0 mm or more, since these bandages are essentially capable of absorbing the amount of liquid secreted from the skin and possible wounds.

Another type of bandage consisting of a combination of the above-mentioned types of bandages is the one known from the above-mentioned DK Published Application 157 899, in which the bandage has an adhesive layer consisting of various types of adhesives arranged juxtaposed in a pattern.

DK Published Application 147 226 (corresponding to U.S. Pat. No. 3,982,328) mentions a bandage which comprises an adhesive layer, a film layer and a flexible layer interposed therebetween.

Like the previously mentioned adhesive layers, the adhesive layer may e.g. contain rubber-like elastomers and liquid absorbing hydrocolloid. The foam layer is a non-compressed semi-open cell layer of e.g. polyurethane which, in addition to being flexible, can also be elastic.

The film layer has a water vapor permeable water impermeable flexible polymer film, such as polyurethane.

Such bandages containing a foam layer may have an overall thickness of down to about 0.6 mm.

A common feature of all the above-mentioned bandages is that they are relatively thin, i.e. thinner than 3.0 mm and in particular thinner than 1.0 mm. Furthermore, they are flexible and frequently elastic so that when being used they can be shaped and conform to the bends and shapes of the skin surface.

The elastic property of the bandages is very essential, because it is precisely this property which enables a bandage to conform to the skin upon movements and the like, and moreover the elasticity of a bandage is of great importance for the comfort when using it.

For a bandage to have a sufficient elasticity to satisfy the functional requirements, as stated above, it is essential that each individual one of the constituent layers is sufficiently elastic, since it is the least elastic layer that determines the elasticity of the assembled product.

The elasticity of the non-adhesive film usually determines the elasticity of the entire dressing, in particular in case of the quite thin dressings, because the adhesive mass is relatively more elastic than even the most elastic non-adhesive polymer film.

Foam layers frequently also possess a sufficient elasticity, in particular the non-compressed foam layers. Bandages containing a polymer foam layer are frequently just as elastic as bandages without a foam layer.

The film layer on bandages with a foam layer and bandages without a foam layer, respectively, serve several purposes.

The film layer on bandages having a foam layer serves inter alia to strengthen the foam layer, cf. DK Published Application 147 226, page 5, lines 9–10.

The film layer on bandages without a foam layer, i.e. where the film layer is in direct contact with the adhesive layer, serves to cover the adhesive face facing away from the skin, so that clothes and other objects do not stick to the adhesive.

Whether or not the bandage has a foam layer, the film serves to protect against contaminations and ingress of bacteria, etc. and another essential purpose of the film is to impart a smooth surface to the bandage.

In the use of the bandage, the film is subjected to several wear forces, such as rubbing against clothes or other objects, tension and stretching as caused by the movements of the user, as well as removal of the bandage.

Thus, it is very important that the film has a sufficient strength to resist these external impacts.

It is thus clear that the most important properties of the film are that it must be elastic and wear resistant.

Both the elasticity and strength properties depend upon the composition of the material and the thickness of the film layer, the elasticity of the film decreasing with increasing thickness, and the strength of the film increasing with increasing thickness. Thus, it has been necessary to weigh the desired elasticity and strength properties.

The non-adhesive films in known dressings of the type described in the opening paragraph thus typically have a thickness of 20–40 μm. Films in this thickness range of a material having a reasonable elasticity can thus essentially satisfy the requirements made both of the elasticity and the wear strength.

The film materials most used are different polyurethanes, which are selected in particular because of their excellent elastic properties and possibly water vapor permeability properties, but also other polymer types, in particular elastomers, are used as non-adhesive films in dressings.

The more elastic a film in a given thickness is, the lower hardness the film material has.

The non-adhesive film used for the known dressings thus consists of a polymer material which is relatively soft either per se or after addition of a plasticizer.

The known dressings consisting of a skin friendly pressure-sensitive adhesive layer and a non-adhesive, relatively soft film, optionally with an elastic foam material layer interposed therebetween, thus have a good flexibility, and the known dressings in which the adhesive layer or the sum of the adhesive layer and the foam layer is 2.0 mm or thinner, have a particularly good flexibility and elasticity, so that they can easily conform to the body to provide great comfort in use.

However, the existing dressings have the drawback that after some time they very frequently roll off completely or partly. This drawback is caused by the fact that in addition to the desirable elasticity, the non-adhesive, relatively soft film also exhibits a high friction in particular with relation to skin, leather, plastics and certain fabrics. In case of external forces, such as friction against articles, clothing or other skin surfaces, the edges of the dressing thus work loose and roll up, causing the adhesive layer to turn away from the skin surface to which it is intended to adhere so that instead it sticks to garments and the like, whereby the dressing is easily torn off or rolled up completely or the foam layer is torn to pieces.

This is a long-known problem, but the only known solution proposed is the one mentioned in EP Patent Application 409 587, in which the employed non-adhesive film is embossed in relief so that the bandage surface area offering resistance upon rubbing against another plain surface is significantly diminished. The coefficient of friction between the embossed bandage surface and a given plane surface, e.g. a non-woven fabric surface, is thus unchanged, but since the contact area is reduced, the resulting friction is likewise reduced.

However, the embossed bandage surface only gives rise to reduced friction upon rubbing against plain or approximately plain surface. Rubbing against irregular surfaces, such as certain knitted or woven fabric surfaces, frequently causes the resulting friction to be considerably greater than if the bandage surface was not embossed. Additionally, protruding parts and edges on, e.g., garments or footwear can very easily grip the bosses and thus cause the bandage to be removed.

Furthermore, the embossed areas in the bandage frequently collect dirt and bacteria, which is very inexpedient and inacceptable to the users.

An essential reason why no other solutions have been developed, as far as is known, is presumably that the elastic property of the dressing has been given priority, because lack of said property would involve even easier undesirable removal of the dressing.

In an attempt at solving the above-mentioned problem of friction, the inventors of the present invention tested, polymer materials having a greater hardness than the materials normally used operated as non-adhesive films in a dressing. As might expected, it was found that the surface friction of the non-adhesive film decreased with increasing hardness of the material, but at the same time the elasticity decreased so drastically that the selection of a polymer material having a hardness giving even a tolerably acceptable low value of friction resulted in such an inelastic polymer film that in the employed thicknesses for use for dressings, it would be quite inapplicable. To obtain even a tolerably acceptable elasticity, it was thus found that the film of the higher hardness should be thinner than 10 μm and preferably 5 μm or less.

When testing a dressing consisting of an adhesive layer and a film with a higher hardness in a thickness of 10 μm or less, it was found that the film tore easily in use, because it did not possess a sufficient strength or elasticity to conform to the movements of the skin or to absorb other effects occurring in use, and it was simultaneously found that large areas, in particular edge areas, were torn in use.

It was additionally found that the dressing having the very thin and relatively hard film was significantly more difficult to remove than the known dressings, because the film broke during removal and thus was not capable of holding the adhesive material together, which was left on the skin in major and minor spots.

OBJECTIVE OF THE INVENTION

The object of the present invention is thus to provide a dressing which comprises an elastic adhesive layer and a non-adhesive film and optionally an elastic foam layer interposed between these, and which has a sufficient elasticity to conform to the skin surfaces of the body, follow the skin during movement, and where the non-adhesive film has a sufficient wear strength to absorb the forces to which the product is subjected in use, and where the non-adhesive film additionally has a surface of less friction than the surface on existing dressings.

Another object of the present invention is to provide an elastic dressing comprising an adhesive layer and a non-adhesive film and optionally a foam layer, which dressing does not break easily in use or during removal of the product, and which has a dynamic friction of less than 5N, preferably less than 4N, and in particular a friction of less than 3N, measured as stated below.

A third object of the present invention is to provide a flexible dressing having a low surface friction, where the non-adhesive film has a sufficient mechanical strength to resist the wear to which it is subjected in the use of the product.

DESCRIPTION OF THE INVENTION

These objects are achieved by the dressing of the invention, which is characterized by the features described below.

Thus, it has surprisingly been found that by applying a film layer of a polymer material having a relatively low hardness between the adhesive layer and a film having a thickness of 10 μm or less of a material having a higher hardness, the film of the higher hardness does not break easily in use or upon removal of the product.

It has moreover surprisingly been found that the dressing of the invention provides a product having a high flexibility and simultaneously a low surface friction.

Additionally, it has surprisingly been found that the dressing of the invention provides a product which has a sufficient mechanical strength to resist wear in use.

Thus, the present invention has made it possible to achieve a dressing having a lower surface friction than the known dressings, while essentially retaining both the essential elastic property and the essential wear strength.

As mentioned, the dressing of the invention comprises an adhesive layer coated on one side with a polymer film, optionally with an intermediate polymer foam layer, said polymer film consisting of an uppermost film layer of a material having a relatively high hardness and a lowermost film layer consisting of a material having a relatively low hardness.

The film layer may have an overall thickness of between 20 and 80 μm, preferably between 25 and 35 μm, and particularly about 27 μm and an $E_{50\%}$ value of between 1.0 and 2.5N, preferably between 1.0 and 2.0N.

The $E_{50\%}$ value is an expression of the force used for stretching the film layer and is thus an expression of the flexibility of the film layer. For some materials, the $E_{50\%}$ value is very dependent on the temperature at which it is measured. The $E_{50\%}$ value is moreover linearly dependent on the thickness of the material.

$E_{50\%}$ is measured according to DS/ISO 1184, the test piece being constructed as a dumb bell sample having a width of 12.5 mm, the initial spacing between the jaws being 100 mm, and the pull rate being 100 mm/min. All measurements are made at about 20° C.

The $E_{50\%}$ values of the non-adhesive film layers used for the dressings of the invention have been found to be of the same order as for the non-adhesive film layers used in the known dressings having the higher surface friction.

The desired water vapor permeability greatly depends upon which type of adhesive and which thickness of the adhesive the film is to be combined with, and upon whether an intermediate foam layer is provided and the thickness and nature of this optional foam layer. By nature is meant the porosity of the foam, and whether it is open cell, semi-open cell or closed cell foam. Thus, the water vapor permeability of the film may be between 2 and 20,000 $g/m^2/24h$.

In case of hydrogel adhesives, the film layer can thus have a water vapor permeability of as low as 2 $g/m^2/24h$, but a water vapor permeability of above 500/$g/m^2/24h$ is preferred in case of the non-saturated hydrogel adhesives, while the film is preferably to have a water vapor permeability of above 1000 $g/m^2/24h$ when used in combination with an essentially nonliquid absorbing adhesive.

For use in connection with a hydrocolloid adhesive, a water vapor permeability of above 500 $g/m^2/24h$ is preferred.

The adhesive layer may be of any pressure-sensitive adhesive material which lends itself for use on skin. The adhesive layer may, e.g. comprise rubber, rubber-like synthetic homopolymers, copolymers or block polymers, polyacrylate and copolymerisates thereof, polyurethane, silicone, polyisobutylene, polyvinyl ether and natural or synthetic resins or mixtures of these. The adhesive layer may moreover be a hydrogel adhesive of e.g. one of the previously mentioned types. The adhesive matrix may additionally contain various additives, such as plasticizers, thickeners, alcohols and others, as well as optionally hydrocolloids and/or various drugs, such as antiseptics, hormones, nicotine, etc.

These adhesive materials are generally known and further information on these can be found e.g., in the previously mentioned publications.

The adhesive layer may be continuous and cover the entire one side of the dressing. It may discontinuous in strips or points or cover an edge width of the product, or the adhesive layer may consist of two or more different adhesives arranged juxtaposed in a pattern, as known from DK Published Application 157 899. The adhesive layer preferably has a thickness not exceeding 3 mm and in particular a thickness not exceeding 2 mm. A thickness of between 0.3 and 1.1 mm is particularly preferred.

If the dressing has an intermediate foam layer, this layer may, e.g., consist of an open celled, a semi-open celled or a closed celled foam material of, e.g., polyurethane, polyacrylate or natural rubber. Such an intermediate foam layer preferably has a thickness of between 0.3–1.5 mm.

The lowermost film layer of the polymeric non-adhesive film consists of a material such as polyurethane, polyethylene, polybutadiene, polyvinyl chloride, polyvinylidene chloride, polyvinyl alcohol, polyacrylate, polysulphone, polystyrene, polypropylene, polyamide, ethylene-vinylacetate copolymer, polyester, polycarbonate, polyvinyl fluoride, copolyester ether, synthetic or natural rubbers, silicone and mixtures of these. Particularly preferred are elastomers, such as polyurethane, copolyester ether and synthetic or natural rubbers.

The lowermost film layer may additionally contain various additives, such as plasticizers, e.g., dioctyl adipate, as well as fillers, e.g., $SiO_2$, and pigments.

The lowermost film layer is of a material which, either per se or after addition of a plasticizer, has a relatively low hardness and is thus very elastic.

The lowermost film layer preferably has a thickness of between 15 and 70 µm, in particular of between 15 and 35 µm. It can be an aromatic polyether-based polyurethane having a hardness of 80 A shore or less, containing up to 5% $SiO_2$ and up to 7% dioctyl adipate and a thickness between 17 and 25 µm.

If a greater water vapor permeability through the dressing is desired, the lowermost film may optionally be discontinuous, i.e., the film layer does not cover the entire face, but the film layer is preferably to cover at least 50% of the face, for instance at least about 85%, and in particular it is advantageous if each of the non-covered areas does not have an extent of more than 25 $mm^2$, preferably less than 10 $mm^2$.

The uppermost film layer of the polymeric non-adhesive film consists of a material such as polyurethane, polyethylene, polybutadiene, polyvinyl chloride, polyvinylidene chloride, polyvinyl alcohol, polyacrylate, potysulphone, polystyrene, polypropylene, polyamide, ethylene-vinylacetate copolymer, polyester, polycarbonate, polyvinyl fluoride, copolyester ether, synthetic or natural rubbers, silicone and mixtures of these. Particularly preferred are elastomers, such as polyurethane, copolyester ether and synthetic or natural rubbers.

The uppermost film layer may additionally contain various additives, such as an antiblocking agent, e.g., $SiO_2$, friction-reducing agents, such as $SiO_2$ and talc which have well-known but only less friction-reducing effects, as well as optionally minor amounts of a plasticizer.

The uppermost film layer is of a material having a relatively high hardness and a thickness of up to 10 µm, in particular of between 2 and 5 µm. This material of the high hardness, i.e., a hardness higher than the hardness of the lowermost film material, is thus less elastic than the material of the lower hardness, but since the thickness of the uppermost film layer is smaller than the thickness of the lowermost film layer, the resulting elasticity of the sum of the two film layers is essentially of the same order as the elasticity of the film layers which are used in the known dressings. It can be an aromatic polyester-based polyurethane having a hardness of 65 A shore or above, containing 5–20% $SiO_2$, and having a layer thickness of 2–10 µ.

On its adhesive side, the dressing may be provided with a removable cover layer, which can optionally be formed in a manner such that the product can be applied without the adhesive layer being touched by the fingers, as is known from, e.g., NO Published Application 156 035 and from EP Patent Application 189 999.

The dressing may moreover be covered on the film side with a removable cover layer, as is known from, e.g., WO Patent Application 90/01915. If the dressing is very thin, such a cover layer is particularly desirable because it imparts a stiffness to the product which makes it easier to position the product at the moment of application, while preventing the product from sticking to itself.

The dressing of the invention can be manufactured in several different ways in principle. The manufacture can, e.g., take place in the following steps:

a) The polymer material for the uppermost film layer is dissolved in a suitable solvent, and optional additives are admixed, following which the mixture is applied in a thin layer to a suitable carrier material which easily releases the finished polymer and is dried.

b) The polymer material for the lowermost film layer is dissolved in a suitable solvent, and optional additives are admixed, following which the mixture is applied (optionally in a pattern), on the uppermost film and is dried.

c) An adhesive material is applied to the film layer, with a foam layer optionally interposed between the adhesive material and the film material, and the adhesive material is optionally covered with a removable release layer.

d) The skin sheets are punched after optional bevelling, e.g., as mentioned in DK Published Application 154 747.

The amount of the mixture applied in b) is of an order such that the lowermost film layer after drying is thicker than the uppermost film layer, the uppermost film layer being preferably smaller than 10 µm.

The application of the adhesive material stated in c) can take place in several ways, e.g. by a hot melt method, including extrusion or spreading of the adhesive or by coating with a dissolved or emulsified adhesive material followed by drying.

The process described in a)–d) can take place in-line, or each step can be performed separately, so that the carrier material with the applied material is rolled up after one or more of the stated steps, optionally after application of a removable cover paper layer.

If such cover paper has been applied, it is removed again when the carrier material is rolled out at the beginning of the next step, it being unnecessary to remove the cover paper at the beginning of step c); because bevelling and punching can be performed very well while this cover paper is on.

The dressing of the invention is useful for all forms of treatment of skin surfaces, and it is particularly useful in the situation where the product is particularly subjected to external impacts, such as friction against other objects and wear.

The dressing of the invention is thus particularly useful for ambulant treatment where the patients are not physically impaired, for treatment of in bedridden patients, since these patients as well as all other humans are restless in their sleep in many cases, as well as for prophylactic treatment of exposed skin areas, such as heels, elbows, knees and palms.

BRIEF DESCRIPTION OF THE DRAWINGS

The invention will be described more fully below with reference to examples and the drawing, in which.

DETAILED DESCRIPTION OF THE DRAWINGS

Figure 1:
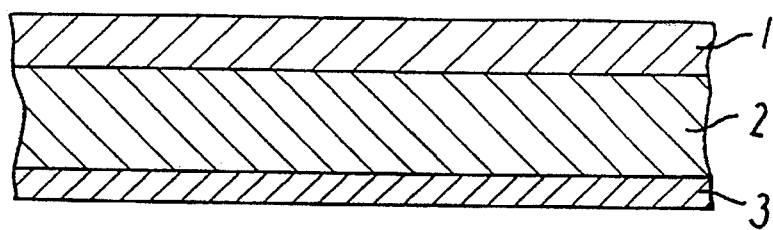
FIG. 1 shows a cross-section of a known dressing.

The known dressing shown in FIG. 1 consists of a non-adhesive polymer film (1), a skin friendly pressure-sensitive adhesive (2) and a removable cover layer (3). In some of the known dressings, a foam layer (not shown) is moreover interposed between the film layer (1) and the adhesive layer (2).

Figure 2:
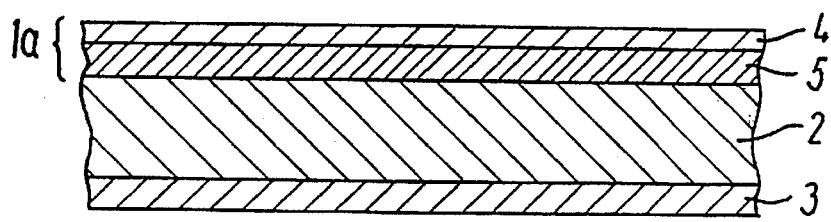
FIG. 2 shows a cross-section of a dressing according to the invention.

The dressing of the invention, which is illustrated in FIG. 2, likewise consists of a non-adhesive polymer film (1a), a skin friendly pressure-sensitive adhesive (2) and a removable cover layer (3). In contrast to the dressing shown in FIG. 1, the non-adhesive film (1a) is a laminate consisting of an uppermost film layer (4) and a lowermost film layer (5).

The uppermost film layer (4) is of a relatively hard material, and the surface of the film (4) has a relatively low friction.

The lowermost film layer (5) is of a relatively soft material and is thicker than the uppermost film layer (4).

As mentioned before, the two film layers (4, 5) may consist of a large number of various materials, and the same or a different polymer may be used as the basic component in the two layers. Preferably, polyurethane is used in both layers.

The two materials must have a sufficient affinity to each other so that they do not delaminate in use.

The materials are additionally selected on the basis of the water vapor permeability desired.

It will be possible to a person skilled in the field to find useful materials by an ordinary optimization process which give the desired water vapor permeability and which do not delaminte.

Figure 3:
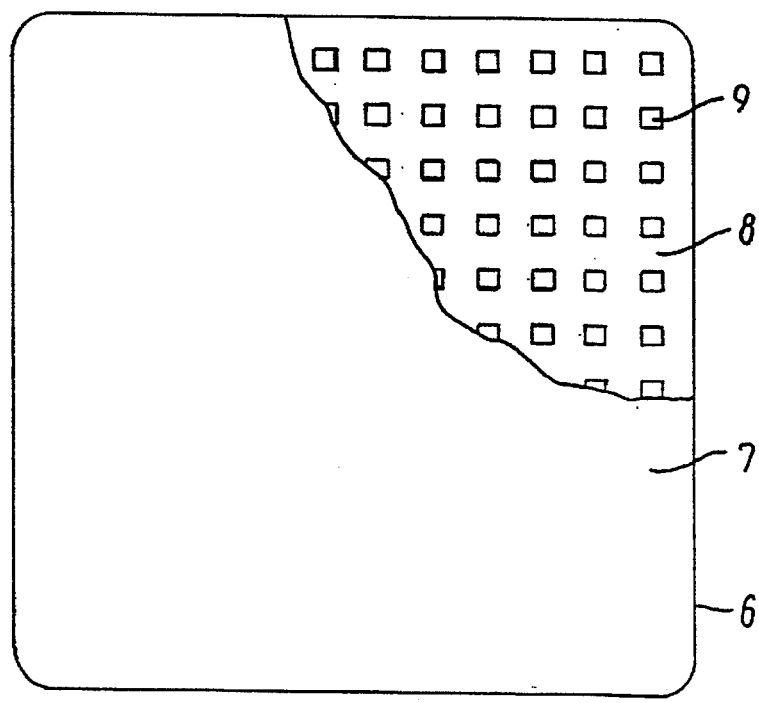
FIG. 3 is a top view of an embodiment of a dressing according to the invention with parts of the uppermost film layer removed.

In a special embodiment of the dressing of the invention, see FIG. 3, the dressing 6 consists of an adhesive (not shown) having a removable cover layer (not shown) as well as an uppermost film layer (7) with a surface which has a low friction, and a lowermost film layer (8) which is applied discontinuously so that there are areas (9) which are not covered by the lowermost film.

With a bandage like the one shown in FIG. 3 it is possible to obtain a dressing having a particularly great water vapor permeability, and a great water vapor permeability is obtained in particular if the film layer (7) consists of a material which is very water vapor permeable per se.

The areas which are not covered by the lowermost film in the special embodiment, do not give rise to any significant reduction in the wear strength of the dressing, in particular not if their extent is limited, and the overall area not covered by the lowermost film consitutes less than 50%, and in particular not if it just constitutes about 15% of the face area like in the embodiment shown in FIG. 3, or less.

Additionally, it is particularly advantageous if the individual non-covered areas have an extent of 25 mm$^2$ or below, and in particular below 10 mm$^2$.

Figure 4:
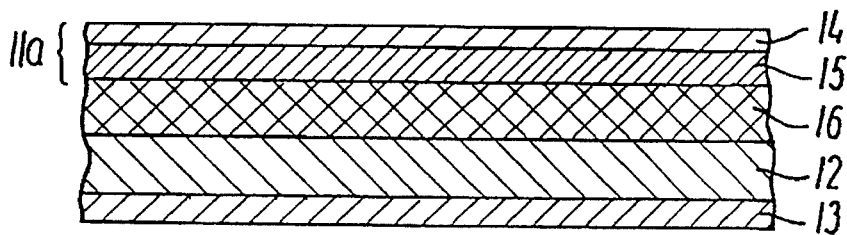
FIG. 4 shows a cross-section of a second embodiment of the bandage according to the invention, and FIG. 5 schematically shows an apparatus for in-line production of the dressing according to the invention.

The bandange of the invention shown in FIG. 4 consists of a skin friendly pressure-sensitive adhesive 12, which is coated with a removable cover layer (13) on one side and is coated on the other side with a foam layer (16) of, e.g., semi-open celled polyurethane and a non-adhesive polymer film (11a) consisting of an uppermost film layer (14) and a lowermost film layer (15).

The layers 12, 13, 14 and 15 correspond to the layers 2, 3, 4 and 5 in the bandage shown in FIG. 2.

Figure 5:
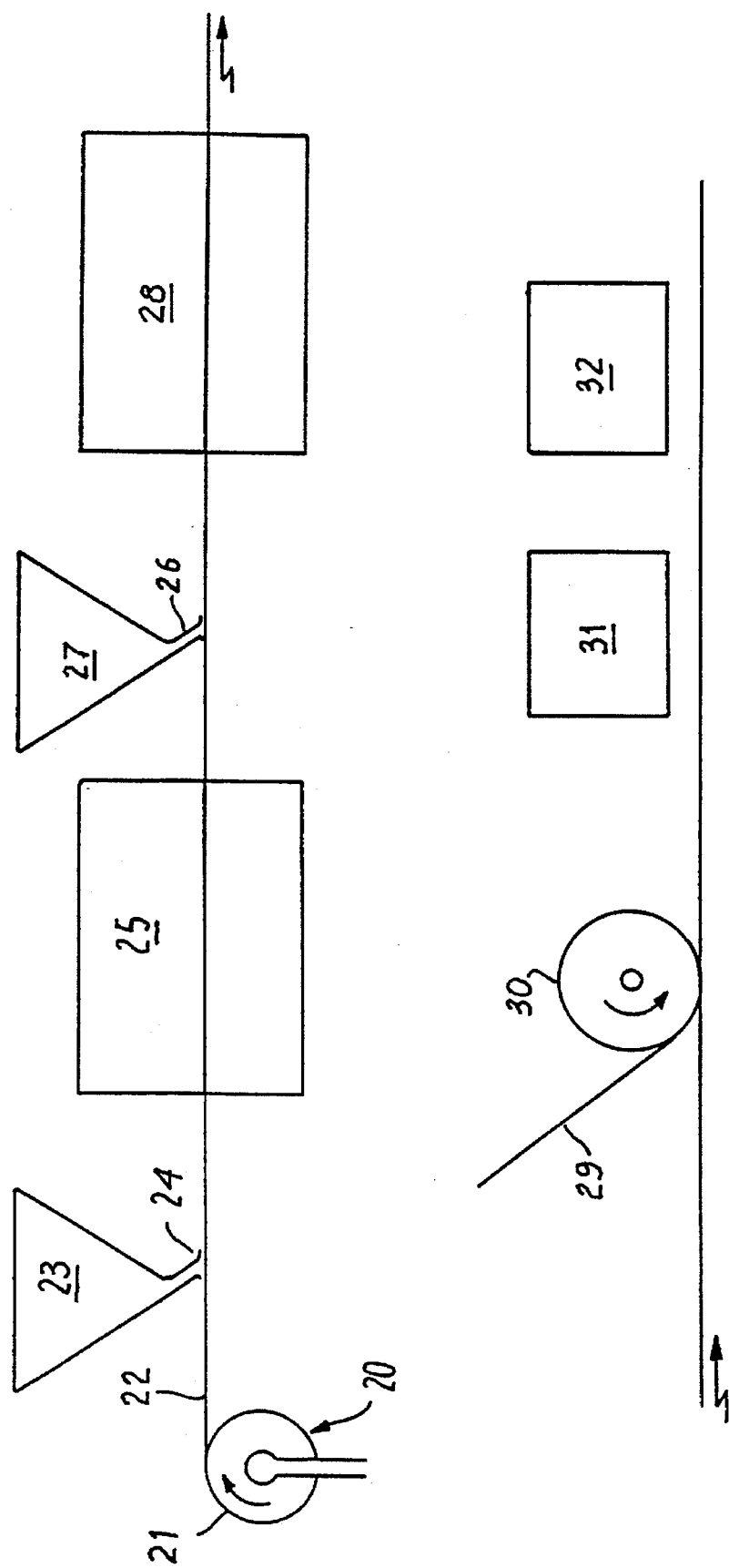

The apparatus shown in FIG. 5 comprises a means (20) on which a roll (21) of carrier material (22) can be mounted, as well as a means (not shown) capable of pulling the carrier material through the various treatment stations. The carrier material (22) is pulled off the roll (11), past an application means (24) in which the uppermost film layer is applied, the applied material which consists of a dissolved polymer and optional additives, fillers, etc., being conveyed from a container (23) to the application means (24). The carrier material with the uppermost film layer is pulled further on through a drying station (25) and past a second application means (26), which receives application material from a container (27) containing material for the lowermost film layer which consists of a dissolved polymer and optional additives, fillers, etc. The carrier material with the two film layers is pulled past a second drying station (28), and then an adhesive layer (29) is fed from an adhesive roll (not shown), said adhesive layer being provided with a removable cover layer on the side facing away from the laminate, said adhesive layer being applied to the film layer by means of an application roller (30), with optional addition of heat to improve the bonding between the adhesive layer and the film laminate. The carrier material is moved further on past a bevelling station (31) and a punching station (32).

If desired, a station may be inserted after the drying station (28) for applying a foam layer, which can be bonded to the film layer by slight heating.

EXAMPLE

The samples shown in FIG. 1 were manufactured.

S stands for an aromatic polyether-based polyurethane ESTANE® 5714 having a hardness of 80 A shore.

H stands for an aromatic polyester-based polyurethane ESTANE® 5707 having a hardness of 95 A shore.

The ESTANE® products are available from BF Goodrich Chemical, Belgium.

Syloid® (Syloid® ED-30) is an $SiO_2$ product available from W. R. Grace, and

DOA stands for dioctyl adipate.

All percentages are per cent by weight, unless otherwise stated.

The samples were tested, and the results appear from table 2.

The following methods of measurement were used:

Force for 50% elongation ($E_{50\%}$).

$E_{50\%}$ was measured according to DS/ISO 1184, the test piece being constructed as a dumb bell sample having a width of 12.5 mm, the initial spacing the jaws being 100 mm, and the pull rate being 100 mm/min. The measurements were performed at about 20° C.

Elasticity

The test piece was elongated to 50% elongation, and then the application of force was removed. This was repeated 5 times. The elasticity was calculated as:

$$\text{Elasticity} = \frac{E_{50\%}, \text{5th time}}{E_{50\%}, \text{1st time}} \times 100\%$$

$E_{50\%}$, 1st time and $E_{50\%}$, 5th time were measured according to DS/ISO 1184, the test piece being constructed a dumb bell sample having a width of 12.5 mm, the initial spacing between the jaws being 100 mm, and the pull rate being 510 mm/min. The measurements were performed at about 20° C.

Tensile strength/Elongation at break

Tensile strength and elongation at break were measured according to DS/ISO 1184, the test piece being constructed as a dumb bell sample having a width of 12.5 mm, the initial spacing between the jaws being 100 mm, and the pull rate being 100 mm/min. The measurement were performed at about 20° C.

Friction

The friction was measured as the dynamic friction according to ISO 8295, 1986, the base used being a teflon coated glass tissue of the type: Acoflon G 13 A from Aco-plast A/S, Helsingør, DK, the weight of the carriage being 500 g.

Water Vapor Permeability

The water vapor permeability of the films was measured by water contact with the soft PU film as described in ASTM E96-80.

The stated values were measured on a circular test piece with a diameter of 20 mm and at a temperature of 37° C. and a relative air humility of 30%.

Results

It will be seen clearly from the results in table 2 that the surface friction of ESTANE® 5707 (samples 5, 6, 7 and 8) is considerably lower than of the softer ESTANE® 5714 (samples 1 and 2).

On the other hand, the $E_{50\%}$ values of the hard ESTANE alone are inacceptably high (sample 3).

As mentioned before, the $E_{50\%}$ value of the non-adhesive film is of great importance for the flexibility of the dressing.

In the samples of the invention, in which the non-adhesive film consists of an uppermost hard material and a lowermost soft material (samples 5, 6, 7 and 8), $E_{50\%}$ is at the same level as that obtained by using a relatively soft material of the type employed in the known dressings (samples 1 and 2).

The $E_{50\%}$ value of sample no. 9 according to the invention is somewhat higher, but still within the acceptable limit.

With the relatively hard film layer but without a laminated lowermost film layer and in a thickness of 10 μm (sample 4, the $E_{50\%}$ value is at the same level as for the samples 1 and 2. The $E_{50\%}$ value of sample 4 is thus quite good, but on the other hand the tensile strength is inacceptably low.

Thus, the products of the invention (samples 5, 6, 7, 8 and 9) have a reduced surface friction with respect to the known products (samples 1 and 2), while the flexibility, elasticity, tensile strength and elongation at break are kept at the same level.

TABLE 1

| Samples No. | Lowermost film layer | Uppermost film layer |
| --- | --- | --- |
| 1 | S + 5% syloid - 27 μm | — |
| 2 | S + 4% syloid, 7% DOA - 27 μm | — |
| 3 | — | H + 20% syloid - 27 μm |
| 4 | — | H + 20% syloid - 10 μm |
| 5 | S + 4% syloid, 7% DOA - 24 μm | H + 5% syloid - 3 μm |
| 6 | S + 4% syloid, 7% DOA - 24 μm | H + 10% syloid - 3 μm |
| 7 | S + 4% syloid, 7% DOA - 24 μm | H + 20% syloid - 3 μm |
| 8 | S + 4% syloid, 7% DOA - 24 μm | H + 20% syloid - 3 μm |
| 9 | S + 4% syloid, 7% DOA - 17 μm | H + 20% syloid - 10 μm |

TABLE 2

| | Friction (N) | $E_{50\%}$ (N) | Elasticity (%) | Tensile Strength (N) | Elongation at Break (%) | Water Vapour Permeability (g/m² 24 h) |
| --- | --- | --- | --- | --- | --- | --- |
| | 3* | 3* | 3* | 3* | 3* | 4* |
| | ±10** | ±3** | ±3** | ±15** | ±10** | ±2** |
| 1 | 7.6 | 1.6 | 92 | 10.1 | 491 | |
| 2 | 10.0 | 1.4 | 92 | 5.4 | 487 | 1448 |
| 3 | 1.6 | 3.6 | 81 | 5.2 | 148 | 1669 |
| 4 | 1.6 | 1.4 | 84 | 1.7 | 153 | |
| 5 | 2.2 | 1.7 | 91 | 7.6 | 468 | |
| 6. | 2.4 | 1.8 | 92 | 8.3 | 487 | |
| 7 | 1.6 | 1.9 | 91 | 8.2 | 493 | 1278 |
| 8 | 2.4 | 1.8 | 86 | 7.6 | 474 | |
| 9 | 1.6 | 2.3 | 90 | 8.4 | 487 | |

*Average of (number of samples)
**Uncertainty (%)

User Test—Comparative Example

Two dressings were moreover manufactured, one according to the invention, hereinafter called A, and one according to the prior art, hereinafter called B. The dressings consisted of a 1.00 mm thick adhesive layer and a 27 μm thick film layer.

The adhesive composition was identical for the two dressings, viz. the following:

| | |
| --- | --- |
| Elastomer | 24.10% |
| Resin | 35.10% |
| Plasticizer | 9.75% |
| Antioxidant | 1.00% |
| Hydrocolloid | 30.00% |

The components for the adhesive matrix were mixed with heating to 135° C.

Thus, dressing A according to the invention consisted of a 1.00 mm thick adhesive layer, as stated above, as well as a film material coated thereon and having a composition like the film sample no. 7 previously stated (see table 1).

Dressing B according to the prior art consisted of a 1.00 mm thick adhesive layer, as stated above, and a film layer coated thereon and having a composition like the previously stated film sample no. 1 (see table 1).

Both faces on both products A and B were coated with a removable cover layer.

The dressings were bevelled under the action of pressure and heat, as described in DK Published Application 154 747, and punched in oval pieces with a surface area of about 22 cm².

The dressings were rested via a user test performed as follows:

100 randomly chosen Compeed® users received a letter of introduction with instructions, a questionnaire as well as one of each of the dressings A and B.

The letter of introduction informed the users that they participated in a development test of plasters.

The instructions read as follows:

1. Place the plaster marked V on the left heel. H1 on the right heel.
2. The area where the plaster is placed must be totally clean and dry, and you must not have used cream within the last 24 hours.
3. It is important that the plasters are placed uniformly on the right and left heels.
4. Remove the paper on both sides of the plaster prior to application.
5. Stretch the skin—tip the foot upwardly prior to application.
6. Apply the plaster carefully. Take special care that the edges adhere firmly.
7. Warm the plaster with the hand for about 1 minute.
8. When one of the plasters loosens, remove both plasters, and complete the questionnaire.
9. Remove the plaster by elongating it along the skin surface.

Result:

35 of the user test participants answered the following questions:

I How did the plasters fit?
II Did the plasters tend to adhere to the stockings?
III Which plaster is the best?

Answer:

Question I

|  | Too badly | Well | Too well |
|---|---|---|---|
| Dressing A | 13% | 78% | 9% |
| Dressing B | 39% | 57% | 4% |

Question II

|  | YES | NO |
|---|---|---|
| Dressing A | 30% | 70% |
| Dressing B | 48% | 52% |

Question III

| Dressing A | 58% |
|---|---|
| Dressing B | 21% |
| Equally good | 21% |

The user test result shows clearly that the dressing of the invention is a better fit and provides a better comfort than the known dressings, and that these improvements are exclusively due to the fact that the dressing of the invention has a smaller surface friction than the dressing of the prior art.

The above-mentioned test therefore shows clearly that the dressing of the invention provides a product which has the advantages stated in the preamble to the description over the known dressings, without this being at the expense of the generally good properties in use.

We claim:

1. A dressing comprising a skin friendly, pressure-sensitive adhesive layer which is coated on one side with a non-adhesive flexible polymer film and characterized in that the polymer film consists of two film layers in the direction away from the adhesive layer, the outermost film layer having a thickness not exceeding 10 μm and being of a material which is hard relative to the innermost film layer and said innermost film layer being thicker than said outermost film layer.

2. A dressing according to claim 1 characterized in that the outermost film layer has a dynamic friction not exceeding 5N.

3. A dressing according to claim 1, characterized in that the innermost film layer has a thickness of between 15 and 70 μm.

4. A dressing according to claim 1, characterized in that the polymer film is liquid impermeable.

5. A dressing according to claim 1, characterized in that the skin friendly adhesive is substantially not liquid absorbing, and that the non-adhesive polymer film has a water vapor permeability of more than 1000 $g/m^2/24h$.

6. A dressing according to claim 1, characterized in that both the outermost and innermost film layers are of polyurethane.

7. A dressing according to claim 1, characterized in that the adhesive layer is continuous.

8. A dressing according to claim 1, characterized in that the adhesive layer is coated, on the side opposite the non-adhesive flexible polymer film, with a removable release layer.

9. A dressing according to claim 1, characterized in that the outermost film layer has a thickness of between 2 and 5 μm and a dynamic friction not exceeding 4N and the innermost film layer has a thickness between 15 and 35 μm.

10. A dressing according to claim 9, characterized in that the outermost film layer has a dynamic friction not exceeding 3N.

11. A dressing according to claim 1, characterized in that the skin friendly adhesive is a hydrocolloid adhesive or an unsaturated hydrogel adhesive, and that the non-adhesive polymer film has a water vapor permeability of more than 500 $g/m^2/24h$.

12. A dressing according to claim 11, characterized in that the non-adhesive polymer film has a water vapor permiability of more than 1000 $g/m^2/24h$.

13. A dressing according to claim 1, characterized in that the innermost film layer is discontinuous covering more than 50% of the adjacent surface of the outermost area and each individual non-covered area has an extent of 25 $mm^2$ or below.

14. A dressing according to claim 13, characterized in that the discontinuous innermost film covers at least about 85% of the adjacent surface of the outermost film area and the individual non-covered areas have an extent below 10 $mm^2$.

15. A dressing according to claim 1, characterized in that the outermost film layer is an elastomeric material selected from the group consisting of polyurethane, copolyester ether, synthetic rubber, natural rubber, and mixtures thereof.

16. A dressing according to claim 15, characterized in that the outermost film layer is of polyurethane and contains an antiblocking agent.

17. A dressing according to claim 16, characterized in that the outermost film layer of an aromatic polyester-based polyurethane having a hardness of 95 A shore or above, containing 5–20% $SiO_2$, and said film layer has a thickness of 2 to 10 μm.

18. A dressing according to claim 1, characterized in that the innermost film layer is an elastomeric material selected from the group consisting of polyurethane, copolyester ether, synthetic rubber, natural rubber and mixtures thereof.

19. A dressing according to claim 18, characterized in that the innermost film layer is of polyurethane containing filler and plasticizer.

20. A dressing according to claim 19, characterized in that the innermost film layer is of an aromatic polyether-based polyurethane having a hardness of 80 A shore or less, containing up to 5% $SiO_2$ and up to 7% dioctyl adipate, and has a thickness of between 17 and 25 μm.

21. A dressing according to claim 18, characterized in that the adhesive has a thickness of up to 3 mm.

22. A dressing according to claim 21, characterized in that the adhesive has a thickness between 0.3 and 2 mm.

* * * * *